US009801935B2

(12) United States Patent
O'Hagan et al.

(10) Patent No.: US 9,801,935 B2
(45) Date of Patent: Oct. 31, 2017

(54) SOLUBLE NEEDLE ARRAYS FOR DELIVERY OF INFLUENZA VACCINES

(71) Applicant: Seqirus UK Limited, Berkshire (GB)

(72) Inventors: Derek O'Hagan, Cambridge, MA (US); Manmohan Singh, Cambridge, MA (US); Sung-Yun Kwon, Cambridge, MA (US)

(73) Assignee: SEQIRUS UK LIMITED, Berkshire (GB)

( * ) Notice: Subject to any disclaimer, the term of this patent is extended or adjusted under 35 U.S.C. 154(b) by 0 days.

(21) Appl. No.: 15/290,349

(22) Filed: Oct. 11, 2016

(65) Prior Publication Data

US 2017/0119872 A1     May 4, 2017

Related U.S. Application Data

(63) Continuation of application No. 13/817,814, filed as application No. PCT/IB2011/002184 on Aug. 19, 2011, now Pat. No. 9,517,205.

(Continued)

(51) Int. Cl.
*A61M 5/158* (2006.01)
*A61K 39/145* (2006.01)
(Continued)

(52) U.S. Cl.
CPC .......... *A61K 39/145* (2013.01); *A61B 17/205* (2013.01); *A61M 37/0015* (2013.01);
(Continued)

(58) Field of Classification Search
None
See application file for complete search history.

(56) References Cited

U.S. PATENT DOCUMENTS

| 7,182,747 B2 | 2/2007 | Kwon |
| 2004/0096455 A1 | 5/2004 | Maa et al. |

(Continued)

FOREIGN PATENT DOCUMENTS

| CA | 2106914 A1 | 3/1994 |
| EP | 0589348 B2 | 5/2012 |

(Continued)

OTHER PUBLICATIONS

Anonymous (2009) "Intradermal Delivery of Vaccines: A review of the literature and the potential for development for use in low- and middle-income countries", World Health Organization (WHO), 94 pages.

(Continued)

*Primary Examiner* — Lakshmi Channavajjala
(74) *Attorney, Agent, or Firm* — Finnegan, Henderson, Farabow, Garrett & Dunner, LLP

(57) ABSTRACT

Influenza vaccines are administered using solid biodegradable microneedles. The microneedles are fabricated from the influenza vaccine in combination with solid excipient(s) and, after penetrating the skin, they dissolve in situ and release the vaccine to the immune system. The influenza vaccine is (i) a purified influenza virus surface antigen vaccine, rather than a live vaccine or a whole-virus or split inactivated vaccine (ii) an influenza vaccine prepared from viruses grown in cell culture, not eggs, (iii) a monovalent influenza vaccine e.g. for immunizing against a pandemic strain, (iv) a bivalent vaccine, (v) a tetravalent or >4-valent vaccine, (vi) a mercury-free vaccine, or (vii) a gelatin-free vaccine.

10 Claims, 7 Drawing Sheets

Related U.S. Application Data

(60) Provisional application No. 61/401,844, filed on Aug. 20, 2010.

(51) Int. Cl.
  *G01N 33/68* (2006.01)
  *A61M 37/00* (2006.01)
  *A61B 17/20* (2006.01)
  *A61K 39/00* (2006.01)
  *A61B 17/00* (2006.01)

(52) U.S. Cl.
  CPC .... *G01N 33/68* (2013.01); *A61B 2017/00004* (2013.01); *A61K 2039/54* (2013.01); *A61K 2039/70* (2013.01); *A61M 2037/0023* (2013.01); *A61M 2037/0046* (2013.01); *A61M 2202/30* (2013.01); *C12N 2760/16134* (2013.01); *C12N 2760/16234* (2013.01); *G01N 2333/11* (2013.01)

(56) References Cited

U.S. PATENT DOCUMENTS

| | | |
|---|---|---|
| 2006/0280644 A1 | 12/2006 | Sellers et al. |
| 2009/0092620 A1 | 4/2009 | Moste et al. |
| 2010/0010199 A1 | 1/2010 | Tsai et al. |
| 2013/0224245 A1 | 8/2013 | Kommareddy et al. |
| 2013/0243841 A1 | 9/2013 | Kommareddy et al. |

FOREIGN PATENT DOCUMENTS

| | | |
|---|---|---|
| WO | WO 2004/105729 A2 | 12/2004 |
| WO | WO 2005/016239 A2 | 2/2005 |
| WO | WO 2005/112463 A2 | 11/2005 |
| WO | WO 2008/032219 A2 | 3/2008 |
| WO | WO 2008/130587 A2 | 10/2008 |
| WO | WO 2010/071918 A1 | 7/2010 |
| WO | WO 2010/078323 A1 | 7/2010 |
| WO | WO 2011/151723 A2 | 12/2011 |
| WO | WO 2011/151726 A2 | 12/2011 |

OTHER PUBLICATIONS

Fluzone (2010) "Product prescribing information", Sanofi pasteur, 24 pages.
GenScript (2008) "Press Release, GenScript antibody service guarantees ELISA titer of 1:20000 and positive western blot results".
International Search Report for International Application No. PCT/IB2011/002184, dated Jan. 17, 2012.
Jordan (2009) "Antigen Measurement using ELISA", The Protein Protocols Handbook, Third Edition Ed. J. M. Walker, Springer.
Kim et al. (2010) "Formulation and coating of microneedles with inactivated influenza virus to improve vaccine stability and immunogenicity", J Control Release, 142(2):187-95.
Kwon et al. (2005) "Rapid Intradermal Drug Delivery by a Dissolvable Micro-Needle patch", Controlled Release Society 32nd Annual Meeting and Exposition Transactions.
Kollipor (2015) "Online Sigma Aldrich catalogue relating to Kolliphor", Sigma Aldrich, 2 pages.
Lee et al. (2008) "Dissolving microneedles for transdermal drug delivery", Biomaterials, 29(13):2113-24.
Notice of Opposition by GlaxoSmithKline, filed in opposition against EP2605792, dated Sep. 9, 2015, 21 pages.
Notice of Opposition by Dr. Gabriele Ahrens, filed in opposition against EP2605792, dated Sep. 10, 2015, 19 pages.
Oh et al. (2006) "Intradermal influenza vaccine delivery using skin-penetrating dissolvable vaccine microneedles", AAPS Annual Meeting and Exposition, 1 page.
Optaflu (2007) "Summary of Product Characteristics". EMEA, 24 pages.
Skountzou et al. (2006) "Transcutaneous immunization with inactivated influenza virus induces protective immune responses", Vaccine, 24(35-36):6110-9.
Sullivan et al. (2010) "Dissolving polymer microneedle patches for influenza vaccination", Nature Medicine 16(8):915-920.
Written Opinion of the International Searching Authority for International Application No. PCT/IB2011/002184.
Yeu-Chun et al. (2010) "Enhanced memory responses to seasonal H1N1 influenza vaccination of the skin with the use of vaccine-coated microneedles", J Infect Dis, (2):190-198.
Agriflu, Novartis Vaccines and Diagnostics, Inc., US Package Insert, 11 pages, Feb. 2013.
Flucelvax, Novartis Vaccines and Diagnostics, Inc., US Package Insert, 14 pages, May 2015.
Fluvirin®, Influenza Virus Vaccine, Novartis Vaccines and Diagnostics Limited, 2015-2016 Formula, 20 pages.
Influvac®, Product Monograph, Solvay Pharma, May 2006.

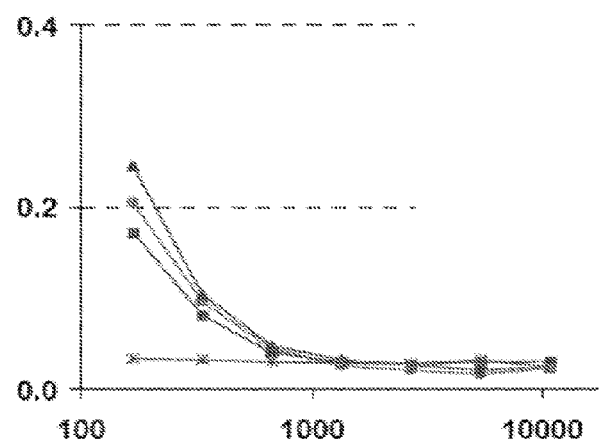
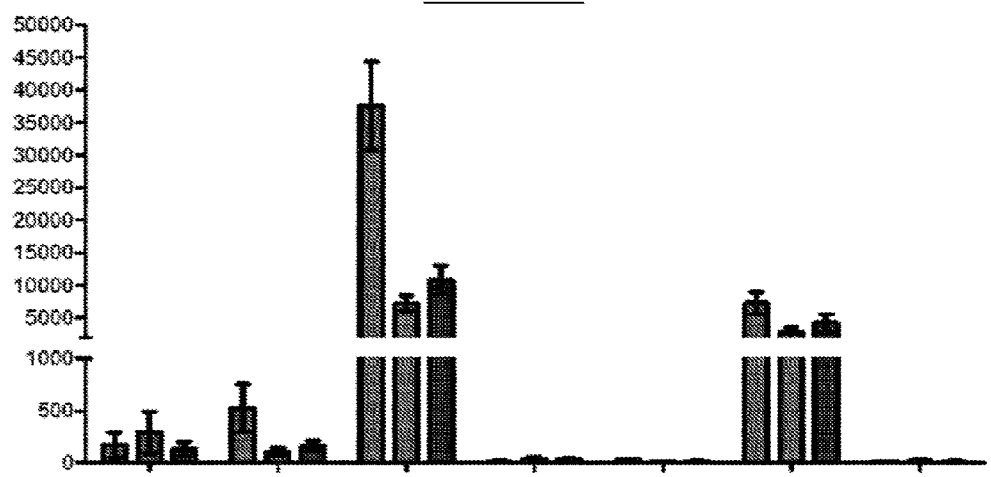

SOLUBLE NEEDLE ARRAYS FOR DELIVERY OF INFLUENZA VACCINES

This application is a continuation of U.S. patent application Ser. No. 13/817,814, filed Jun. 27, 2013, now U.S. Pat. No. 9,517,205, which is a U.S. National Phase patent application of PCT/IB2011/002184, filed Aug. 19, 2011, which claims priority to U.S. Provisional Patent Application No. 61/401,844, filed Aug. 20, 2010, all of which are hereby incorporated by reference in the present disclosure in their entirety.

TECHNICAL FIELD

This invention is in the field of influenza vaccination.

BACKGROUND ART

Various forms of influenza virus vaccine are currently available (e.g. see chapters 17 & 18 of reference 1) and current vaccines are based either on inactivated or live attenuated viruses. Inactivated vaccines are administered by intramuscular or intradermal injection, whereas live vaccines are administered intranasally.

It is an object of the invention to provide a different way of administering inactivated influenza vaccines, and in particular a more convenient way e.g. which does not require medical personnel, and which may thus be sold in an over-the-counter setting.

DISCLOSURE OF THE INVENTION

According to the invention, influenza vaccines are administered using solid biodegradable microneedles. The microneedles are fabricated from the influenza vaccine in combination with solid excipient(s) and, after penetrating the skin, they dissolve in situ and release the vaccine to the immune system. In preferred embodiments the influenza vaccine is (i) a purified influenza virus surface antigen vaccine, rather than a live vaccine or a whole-virus or split inactivated vaccine (ii) an influenza vaccine prepared from viruses grown in cell culture, not eggs, (iii) a monovalent influenza vaccine e.g. for immunising against a pandemic strain, (iv) a bivalent vaccine, (v) a tetravalent or >4-valent vaccine, (vi) a mercury-free vaccine, and/or (vii) a gelatin-free vaccine.

Thus the invention provides a skin patch comprising a plurality of solid biodegradable microneedles, wherein the microneedles comprise a mixture of (i) a biosoluble and biodegradable matrix material and (ii) an influenza vaccine selected from the group consisting of a purified influenza virus surface antigen vaccine, an influenza vaccine prepared from viruses grown in cell culture, a monovalent influenza vaccine, a bivalent vaccine, a tetravalent or >4-valent vaccine, a mercury-free vaccine, and a gelatin-free vaccine. The vaccine can have one or more of these features. This patch can be used to deliver an influenza vaccine to a subject via their skin, and so can be used in a method for raising an immune response in a mammal.

The invention also provides a process for preparing a skin patch comprising a plurality of solid biodegradable microneedles, comprising steps of: (i) mixing a biosoluble and biodegradable matrix material with an influenza vaccine selected from the group consisting of a purified influenza virus surface antigen vaccine, an influenza vaccine prepared from viruses grown in cell culture, a monovalent influenza vaccine, a bivalent vaccine, a tetravalent or >4-valent vaccine, a mercury-free vaccine, and a gelatin-free vaccine; and (ii) adding the mixture from step (i) to a mold containing cavities for forming microneedles.

The invention also provides an aqueous liquid or solid material comprising (i) a biosoluble and biodegradable matrix material and (ii) an influenza vaccine selected from the group consisting of a purified influenza virus surface antigen vaccine, an influenza vaccine prepared from viruses grown in cell culture, a monovalent influenza vaccine, a bivalent vaccine, a tetravalent or >4-valent vaccine, a mercury-free vaccine, and a gelatin-free vaccine. This material is suitable for preparing a patch of the invention.

The invention also provides a skin patch comprising a plurality of solid biodegradable microneedles, wherein the microneedles comprise a mixture of (i) a biosoluble and biodegradable matrix material and (ii) an influenza virus hemagglutinin, wherein the amount of influenza virus hemagglutinin per patch is ≤16 µg per strain. This patch can be used to deliver an inactivated influenza vaccine to a subject via their skin, and so can be used in a method for raising an immune response in a mammal.

The invention also provides a process for preparing a skin patch comprising a plurality of solid biodegradable microneedles, comprising steps of: (i) mixing a biosoluble and biodegradable matrix material with an influenza vaccine; and (ii) adding the mixture from step (i) to a mold containing cavities for forming microneedles, wherein the amount of mixture added in step (ii) provides a patch having ≤16 µg influenza virus hemagglutinin per strain per patch.

The invention also provides an aqueous liquid or solid material comprising (i) a biosoluble and biodegradable matrix material and (ii) an influenza virus hemagglutinin at a concentration of ≤16 µg per strain. This material is suitable for preparing a patch of the invention.

The invention also provides a process for determining the amount of influenza hemagglutinin in a skin patch, wherein (a) the patch comprises a biosoluble & biodegradable matrix material and an influenza vaccine, and (b) the process comprises steps of: (i) dissolving the patch in a solvent to provide a dissolved patch solution; and (ii) assaying hemagglutinin in the dissolved patch solution by enzyme-linked immunosorbent assay (ELISA).

The invention also provides a process for determining the amount of influenza hemagglutinin in a skin patch, wherein (a) the patch comprises a biosoluble & biodegradable matrix material and an influenza vaccine, and (b) the process comprises steps of: (i) dissolving the patch in a solvent to provide a dissolved patch solution; (ii) precipitating proteins in the dissolved patch solution; and (iii) assaying hemagglutinin after precipitation in step (ii).

The Biodegradable Microneedles

Influenza vaccine is delivered via solid biodegradable microneedles.

The microneedles are solid, such that they retain their structural integrity during storage and can penetrate a subject's skin when the patch is applied. The mechanical characteristics which are required for skin penetration depend on the organism in question, but they will usually have sufficient strength to penetrate human skin. Materials for forming suitable solid needles are readily available and these can be tested to determine appropriate concentrations etc. for any particular need.

The microneedles are biosoluble and biodegradable. Thus the solid material dissolves in the skin after the patch is applied, in contrast to the coated metal microneedles used in references 2 & 3. Having dissolved, the material will then be metabolised to give harmless end-products. The timescale for dissolving after applying the patch can vary, but dissolving will typically commence immediately after applying the patch (e.g. within 10 seconds) and may continue for e.g. up to 1 minute, 5 minutes, 10 minutes, 20 minutes, 30 minutes, 1 hour, 5 hours, 10 hours, or 24 hours, until the microneedle has fully dissolved. Materials with suitable in vivo dissolving kinetics are readily available and these can be varied and tested to determine appropriate concentrations etc. for any desired dissolution profile.

Suitable matrix materials for forming the microneedles will typically be biosoluble and biodegradable polymers, and these may comprise one or more carbohydrates. For example, the material may comprise a cellulose, a dextrin, a dextran, a disaccharide, a chitosan, a chitin, etc., or mixtures thereof. Other GRAS materials may also be used.

Suitable celluloses include, but are not limited to, cellulose, sodium carboxymethyl cellulose, hydroxypropyl cellulose, hydroxyethyl cellulose, and hydroxypropyl methylcellulose. Suitable dextrins include, but are not limited to, maltodextrin, cyclodextrin, amylodextrin, icodextrin, yellow dextrin, and white dextrins. Suitable disaccharides include, but are not limited to, sucrose, lactose, maltose, trehalose, turanose, and cellobiose.

Suitable mixtures for forming biosoluble and biodegradable microneedles include, but are not limited to, mixtures of (i) dextrin and trehalose, (ii) sucrose and sodium carboxymethyl cellulose.

The microneedles can penetrate the skin. They should be long enough to penetrate through the epidermis to deliver material into the dermis (i.e. intradermal delivery), but are ideally not so long that they can penetrate into or past the hypodermis. They will typically be 100-2500 μm long e.g. between 1250-1750 μm long, or about 1500 μm. At the time of delivery the tip may penetrate the dermis, but the base of the needle may remain in the epidermis.

The microneedles can have various shapes and geometries. They will typically be tapered with a skin-facing point e.g. shaped as pyramids or cones. A tapered microneedle with a widest diameter of <500 μm is typical.

A single patch will typically include a plurality of microneedles e.g. $\geq 10$, $\geq 20$, $\geq 30$, $\geq 40$, $\geq 50$, $\geq 60$, $\geq 70$, $\geq 80$, $\geq 90$, $\geq 100$, $\geq 200$, $\geq 300$, $\geq 400$, $\geq 50$, $\geq 750$, $\geq 1000$ or more per patch. Where a patch includes a plurality of microneedles, it may comprise a backing layer to which all of the microneedles are attached. A unitary backing layer with $\geq 20$ projecting microneedles is typical. Where a patch includes a plurality of microneedles, these can be arranged in a regular repeating pattern or array, or may be arranged irregularly. A patch will typically have an area of 3 cm$^2$ or less, for example <2 cm$^2$ or <1 cm$^2$. A circular patch with a diameter of between 0.5 cm and 1.5 cm is useful.

The density of microneedles on a patch can vary, but may be $\geq 10$ cm$^{-2}$, $\geq 20$ cm$^{-2}$, $\geq 30$ cm$^2$, $\geq 40$ cm$^{-2}$, $\geq 50$ cm$^{-2}$, $\geq 60$ cm$^{-2}$, $\geq 70$ cm$^{-2}$, $\geq 80$ cm$^{-2}$ or more.

A patch of the invention has a skin-facing inner face and an environment-facing outer face. The inner face may include an adhesive to facilitate adherence to a subject's skin. When present, it is preferably not present on the microneedles themselves i.e. the microneedles are adhesive-free. For example, a patch may have an additional backing which provides an outer adhesive margin for adhering the patch to skin e.g. as seen in sticking plasters or nicotine patches.

Patches as described above can be made by following the techniques and guidance in references 4-9. For instance, a mold with 1.5 mm-long microneedle cavities can be prepared. A matrix material of dextrin and trehalose can be combined with an influenza vaccine and this aqueous material can be centrifugally cast in the mold to form an array of solid microneedles. A cellulose gel can then be cast over the matrix/vaccine film to form a backing layer on the patch. When this layer has dried, it can be removed to give a patch from which the solid microneedles project. Thus a process of the invention may include, after step (ii), further steps of: (iii) letting the mixture set in the mold, to form solid microneedles; (iv) optionally, applying material to the set microneedles to provide a backing layer; and (v) removing the microneedles (and optional backing layer) from the mold.

Patches of the invention may be packaged into individual pouches e.g. sealed under nitrogen, then heat sealed. They should be stored carefully to avoid damage to the microneedles.

Surface Antigen Influenza Vaccines

Some embodiments of the invention use a surface antigen influenza vaccine. Such vaccines contain fewer viral components than a split or whole virion vaccine. They include the surface antigens hemagglutinin and, typically, also neuraminidase. Processes for preparing these proteins in purified form from influenza viruses are well known in the art. The FLUVIRI™, AGRIPPAL™ and INFLUVAC™ products are examples of surface antigen influenza vaccines.

The ability to administer surface antigen influenza vaccines using solid biosoluble biodegradable microneedles is advantageous. Other intradermal needle formats [10] have been found to be incompatible with the high level of residual detergent that can be present in surface antigen influenza vaccines, but the solid biodegradable microneedle format is effective even in these circumstances. Products of the invention may comprise detergent (e.g. a non-ionic detergent) at between 0.0-50 μg per μg of HA, e.g. as described in more detail below.

Where the invention uses a surface antigen influenza vaccine, this virus may have been grown in eggs. The current standard method for influenza virus growth for vaccines uses embryonated SPF hen eggs, with virus being purified from the egg contents (allantoic fluid). If egg-based viral growth is used then one or more amino acids may be introduced into the allantoid fluid of the egg together with the virus [16].

Virus is first grown in eggs. It is then harvested from the infected eggs. Virions can be harvested from the allantoic fluid by various methods. For example, a purification process may involve zonal centrifugation using a linear sucrose gradient solution that includes detergent to disrupt the virions. Antigens may then be purified, after optional dilution, by diafiltration. Chemical means for inactivating a virus include treatment with an effective amount of one or more of the following agents: detergents, formaldehyde, β-propiolactone, methylene blue, psoralen, carboxyfullerene (C60), binary ethylamine, acetyl ethyleneimine, or combinations thereof. Non-chemical methods of viral inactivation are known in the art, such as for example UV light or gamma irradiation.

Other Forms of Influenza Vaccines

Some embodiments of the invention (specifically those which use cell-culture derived antigens, those which are not trivalent, those which are mercury-free, and those which are gelatin-free) are not restricted to using a surface antigen influenza vaccine. These embodiments may thus use whole inactivated virus, split virus, virosomes, live attenuated virus, or recombinant hemagglutinin. These vaccines can easily be distinguished from surface antigen vaccines by testing their antigens e.g. for the presence of extra influenza virus proteins.

Whole inactivated virions can be obtained by harvesting virions from virus-containing fluids (e.g. obtained from eggs or from culture medium) and then treating them as described above. Split virions are obtained by treating purified virions with detergents (e.g. ethyl ether, polysorbate 80, deoxycholate, tri-N-butyl phosphate, Triton X-100, Triton N101, cetyltrimethylammonium bromide, Tergitol NP9, etc.) to produce subvirion preparations, including the 'Tween-ether' splitting process. Methods of splitting influenza viruses, for example are well known in the art e.g. see refs. 11-16, etc. Splitting of the virus is typically carried out by disrupting or fragmenting whole virus, whether infectious or non-infectious with a disrupting concentration of a splitting agent. The disruption results in a full or partial solubilisation of the virus proteins, altering the integrity of the virus. Preferred splitting agents are non-ionic and ionic (e.g. cationic) surfactants e.g. alkylglycosides, alkylthioglycosides, acyl sugars, sulphobetaines, betains, polyoxyethylene-alkylethers, N,N-dialkyl-Glucamides, Hecameg, alkylphenoxy-polyethoxyethanols, NP9, quaternary ammonium compounds, sarcosyl, CTABs (cetyl trimethyl ammonium bromides), tri-N-butyl phosphate, myristyltrimethylammonium salts, lipofectin, lipofectamine, and DOT-MA, the octyl- or non-ylphenoxy polyoxyethanols (e.g. the Triton surfactants, such as Triton X-100 or Triton N101), polyoxyethylene sorbitan esters (the Tween surfactants), polyoxyethylene ethers, polyoxyethlene esters, etc. One useful splitting procedure uses the consecutive effects of sodium deoxycholate and formaldehyde, and splitting can take place during initial virion purification (e.g. in a sucrose density gradient solution). Thus a splitting process can involve clarification of the virion-containing material (to remove non-virion material), concentration of the harvested virions (e.g. using an adsorption method, such as $CaHPC_4$ adsorption), separation of whole virions from non-virion material, splitting of virions using a splitting agent in a density gradient centrifugation step (e.g. using a sucrose gradient that contains a splitting agent such as sodium deoxycholate), and then filtration (e.g. ultrafiltration) to remove undesired materials. Split virions can usefully be resuspended in sodium phosphate-buffered isotonic sodium chloride solution. Examples of split vaccines are the BEGRIVAC™, INTANZA™, FLUARIX™, FLUZONE™ and FLUSHIELD™ products.

Virosomes are nucleic acid free viral-like liposomal particles [17]. They can be prepared by solubilization of virus with a detergent followed by removal of the nucleocapsid and reconstitution of the membrane containing the viral glycoproteins. An alternative method for preparing virosomes involves adding viral membrane glycoproteins to excess amounts of phospholipids, to give liposomes with viral proteins in their membrane.

Live attenuated viruses are obtained from viruses (grown in eggs or in cell culture), but the viruses are not inactivated. Rather, the virus is attenuated ("art") e.g. so as not to produce influenza-like illness in a ferret model of human influenza infection. It may also be a cold-adapted ("ca") strain i.e. it can replicate efficiently at 25° C., a temperature that is restrictive for replication of many wildtype influenza viruses. It may also be temperature-sensitive ("ts") i.e. its replication is restricted at temperatures at which many wild-type influenza viruses grow efficiently (37-39° C.). The cumulative effect of the ca, ts, and att phenotype is that the virus in the attenuated vaccine can replicate in the nasopharynx to induce protective immunity in a typical human patient, but it does not cause disease i.e. it is safe for general administration to the target human population. These viruses can be prepared by purifying virions from virion-containing fluids e.g. after clarification of the fluids by centrifugation, then stabilization with buffer (e.g. containing sucrose, potassium phosphate, and monosodium glutamate). Live vaccines include the FLUMIST™ product. Although live vaccines can be used with the invention, it is preferred to use non-live vaccines.

As an alternative to using antigens obtained from virions, haemagglutinin can be expressed in a recombinant host (e.g. in an insect cell line, such as Sf9, using a baculovirus vector) and used in purified form [18-20] or in the form of virus-like particles (VLPs; e.g. see references 21 & 22).

Influenza Vaccines from Cell Culture

Some embodiments of the invention use influenza vaccine prepared from viruses which were grown in cell culture, rather than in eggs.

When cell culture is used, the viral growth substrate will typically be a cell line of mammalian origin. Suitable mammalian cells of origin include, but are not limited to, hamster, cattle, primate (including humans and monkeys) and dog cells. Various cell types may be used, such as kidney cells, fibroblasts, retinal cells, lung cells, etc. Examples of suitable hamster cells are the cell lines having the names BHK21 or HKCC. Suitable monkey cells are e.g. African green monkey cells, such as kidney cells as in the Vero cell line. Suitable dog cells are e.g. kidney cells, as in the MDCK cell line. Thus suitable cell lines include, but are not limited to: MDCK; CHO; 293T; BHK; Vero; MRC-5; PER.C6; WI-38; etc. Preferred mammalian cell lines for growing influenza viruses include: MDCK cells [23-26], derived from Madin Darby canine kidney; Vero cells [27-29], derived from African green monkey (*Cercopithecus aethiops*) kidney; or PER.C6 cells [30], derived from human embryonic retinoblasts. These cell lines are widely available e.g. from the American Type Cell Culture (ATCC) collection, from the Coriell Cell Repositories, or from the European Collection of Cell Cultures (ECACC). For example, the ATCC supplies various different Vero cells under catalog numbers CCL-81, CCL-81.2, CRL-1586 and CRL-1587, and it supplies MDCK cells under catalog number CCL-34. PER.C6 is available from the ECACC under deposit number 96022940. As a less-preferred alternative to mammalian cell lines, virus can be grown on avian cell lines [e.g. refs. 31-33], including cell lines derived from ducks (e.g. duck retina) or hens. Examples of avian cell lines include avian embryonic stem cells [31,34] and duck retina cells [32]. Suitable avian embryonic stem cells, include the EBx cell line derived from chicken embryonic stem cells, EB45, EB14, and EB14-074 [35]. Chicken embryo fibroblasts (CEF) may also be used.

The most preferred cell lines for growing influenza viruses are MDCK cell lines. The original MDCK cell line is available from the ATCC as CCL-34, but derivatives of this cell line may also be used. For instance, reference 23 discloses a MDCK cell line that was adapted for growth in suspension culture ('MDCK 33016', deposited as DSM ACC 2219). Similarly, reference 36 discloses a MDCK-derived cell line that grows in suspension in serum-free culture ('B-702', deposited as FERM BP-7449). Reference 37 discloses non-tumorigenic MDCK cells, including 'MDCK-S' (ATCC PTA-6500), 'MDCK-SF101' (ATCC PTA-6501), 'MDCK-SF 102' (ATCC PTA-6502) and 'MDCK-SF 103' (PTA-6503). Reference 38 discloses MDCK cell lines with high susceptibility to infection, including 'MDCK.5F1' cells (ATCC CRL-12042). Any of these MDCK cell lines can be used.

Where virus has been grown on a mammalian cell line then products of the invention will advantageously be free from egg proteins (e.g. ovalbumin and ovomucoid) and from chicken DNA, thereby reducing potential allergenicity.

Hemagglutinin in cell-derived products of the invention can have a different glycosylation pattern from the patterns seen in egg-derived viruses. Thus the HA (and other glycoproteins) may include glycoforms that are not seen in chicken eggs. Useful HA includes canine glycoforms.

The absence of egg-derived materials and of chicken glycoforms provides a way in which vaccine prepared from viruses grown in cell culture can be distinguished from egg-derived products.

Where virus has been grown on a cell line then the culture for growth, and also the viral inoculum used to start the culture, will preferably be free from (i.e. will have been tested for and given a negative result for contamination by) herpes simplex virus, respiratory syncytial virus, parainfluenza virus 3, SARS coronavirus, adenovirus, rhinovirus, reoviruses, polyomaviruses, birnaviruses, circoviruses, and/or parvoviruses [39]. Absence of herpes simplex viruses is particularly preferred. For growth on a cell line, such as on MDCK cells, virus may be grown on cells in suspension [23, 40, 41] or in adherent culture. One suitable MDCK cell line for suspension culture is MDCK 33016 (deposited as DSM ACC 2219). As an alternative, microcarrier culture can be used.

Cell lines supporting influenza virus replication are preferably grown in serum-free culture media and/or protein free media. A medium is referred to as a serum-free medium in the context of the present invention in which there are no additives from serum of human or animal origin. Protein-free is understood to mean cultures in which multiplication of the cells occurs with exclusion of proteins, growth factors, other protein additives and non-serum proteins, but can optionally include proteins such as trypsin or other proteases that may be necessary for viral growth. The cells growing in such cultures naturally contain proteins themselves.

Cell lines supporting influenza virus replication are preferably grown below 37° C. [42] during viral replication e.g. 30-36° C., at 31-35° C., or at 33±1° C.

The method for propagating virus in cultured cells generally includes the steps of inoculating the cultured cells with the strain to be cultured, cultivating the infected cells for a desired time period for virus propagation, such as for example as determined by virus titer or antigen expression (e.g. between 24 and 168 hours after inoculation) and collecting the propagated virus. The cultured cells are inoculated with a virus (measured by PFU or $TCID_{50}$) to cell ratio of 1:500 to 1:1, preferably 1:100 to 1:5, more preferably 1:50 to 1:10. The virus is added to a suspension of the cells or is applied to a monolayer of the cells, and the virus is absorbed on the cells for at least 60 minutes but usually less than 300 minutes, preferably between 90 and 240 minutes at 25° C. to 40° C., preferably 28° C. to 37° C. The infected cell culture (e.g. monolayers) may be removed either by freeze-thawing or by enzymatic action to increase the viral content of the harvested culture supernatants. The harvested fluids are then either inactivated or stored frozen. Cultured cells may be infected at a multiplicity of infection ("m.o.i.") of about 0.0001 to 10, preferably 0.002 to 5, more preferably to 0.001 to 2. Still more preferably, the cells are infected at a m.o.i of about 0.01. Infected cells may be harvested 30 to 60 hours post infection. Preferably, the cells are harvested 34 to 48 hours post infection. Still more preferably, the cells are harvested 38 to 40 hours post infection. Proteases (typically trypsin) are generally added during cell culture to allow viral release, and the proteases can be added at any suitable stage during the culture.

A vaccine product including vaccine prepared from cell culture preferably contains less than 10 ng (preferably less than 1 ng, and more preferably less than 100 pg) of residual host cell DNA per dose, although trace amounts of host cell DNA may be present.

It is preferred that the average length of any residual host cell DNA is less than 5000 bp e.g. less than 400 bp, less than 300 bp, less than 200 bp, less than 100 bp, etc.

Contaminating DNA can be removed during vaccine preparation using standard purification procedures e.g. chromatography, etc. Removal of residual host cell DNA can be enhanced by nuclease treatment e.g. by using a DNase. A convenient method for reducing host cell DNA contamination is disclosed in references 43 & 44, involving a two-step treatment, first using a DNase (e.g. Benzonase). which may be used during viral growth, and then a cationic detergent (e.g. CTAB), which may be used during virion disruption. Treatment with an alkylating agent, such as β-propiolactone, can also be used to remove host cell DNA, and advantageously may also be used to inactivate virions [45].

Influenza Vaccine Valency

Some embodiments of the invention use a monovalent influenza vaccine (i.e. it includes hemagglutinin antigen from a single influenza virus strain) but in some embodiments it may be a multivalent vaccine, such as a trivalent vaccine, a tetravalent vaccine, or a >4-valent vaccine (i.e. including hemagglutinin from more than four different influenza virus strains). Monovalent and multivalent vaccines are readily distinguished by testing for multiple HA types, by amino acid sequencing, etc.

A monovalent vaccine is particularly useful for immunising against a pandemic or potentially-pandemic strain, either during a pandemic or in a pre-pandemic situation. Characteristics of these strains are: (a) they contain a new hemagglutinin compared to the hemagglutinins in currently-circulating human strains, i.e. one that has not been evident in the human population for over a decade (e.g. H2), or has not previously been seen at all in the human population (e.g. H5, H6 or H9, that have generally been found only in bird populations), such that the human population will be immunologically naive to the strain's hemagglutinin; (b) they are capable of being transmitted horizontally in the human population; and (c) they are pathogenic to humans. These strains may have any of influenza A HA subtypes H1, H2, H3, H4, H5, H6, H7, H8, H9, H10, H11, H12, H13, H14, H15 or H16. A virus with H5 hemagglutinin type is preferred for immunizing against pandemic influenza, or a H2, H7 or H9 subtype. The invention may protect against one or more of influenza A virus NA subtypes N1, N2, N3, N4, N5, N6, N7, N8 or N9. Thus possible strains include H5N1, H5N3, H9N2, H2N2, H7N1 and H7N7, and any other emerging potentially pandemic strains. In some embodiments, the invention does not use a monovalent vaccine based on a H1N1 strain e.g. it does not use mouse-adapted A/PR/8/34 H1N1 strain.

A multivalent vaccine is more typical in a seasonal setting e.g. a trivalent vaccine is typical, including hemagglutinins from two influenza A virus strains and one influenza B virus strain, such as from a H1N1 influenza A strain, a H3N2 influenza A virus strain, and an influenza B virus strain. A tetravalent vaccine is also useful [46] e.g. including antigens from two influenza A virus strains and two influenza B virus strains, or three influenza A virus strains and one influenza B virus strain. Thus a vaccine may be bivalent, trivalent, tetravalent, etc. Except for monovalent vaccines, it is usual to include hemagglutinin from both influenza A and influenza B virus strains. In vaccines including only two influenza A virus strains, these will usually be one H1 strain (e.g. a H1N1 strain) and one H3 strain (e.g. a H3N2 strain). In some embodiments, however, there may be one pandemic influenza A virus strain and one H1 strain, or one pandemic influenza A virus strain and one H3 strain.

Where a vaccine includes more than one strain of influenza, the different strains are typically grown separately and are mixed after the viruses have been harvested and antigens have been prepared. Thus a process of the invention may include the step of mixing antigens from more than one influenza strain.

As described in reference 46, exemplary tetravalent vaccines can include hemagglutinin from two influenza A virus strains and two influenza B virus strains ('A-A-B-B'), or from three influenza A virus strains and one influenza B virus strain ('A-A-A-B').

Influenza B virus currently does not display different HA subtypes, but influenza B virus strains do fall into two distinct lineages. These lineages emerged in the late 1980s and have HAs which can be antigenically and/or genetically distinguished from each other [47]. Current influenza B virus strains are either B/Victoria/2/87-like or B/Yamagata/16/88-like. Where a vaccine of the invention includes two influenza B strains, this will usually be one B Victoria/2/87-like strain and one B/Yamagata/16/88-like strain. These strains are usually distinguished antigenically, but differences in amino acid sequences have also been described for distinguishing the two lineages e.g. B/Yamagata/16/88-like strains often (but not always) have HA proteins with deletions at amino acid residue 164, numbered relative to the 'Lee40' HA sequence [48].

Preferred A-A-B-B vaccines include hemagglutinins from: (i) a H1N1 strain; (ii) a H3N2 strain; (iii) a B Victoria/2/87-like strain; and (iv) B/Yamagata/16/88-like strain.

In vaccines including three influenza A virus strains, these will usually be one H1 strain (e.g. a H1N1 strain) and two H3 strains (e.g. two H3N2 strains). The two H3 strains will have antigenically distinct HA proteins e.g. one H3N2 strain that cross-reacts with A/Moscow/10/99 and one H3N2 strain that cross-reacts with A/Fujian/41 1/2002. The two H3 strains may be from different clades (clades A, B and C of H3N2 strains are disclosed in reference 49). In some embodiments, however, one of these strains (i.e. H1, or one of the two H3 strains) may be replaced by a pandemic strain.

Thus one preferred A-A-A-B vaccine includes hemagglutinins from: (i) a H1N1 strain; (ii) a A/Moscow/10/99-like H3N2 strain; (iii) a A/Fujian/41 1/2002-like H3N2 strain; and (iv) an influenza B virus strain, which may be B/Victoria/2/87-like or B/Yamagata/16/88-like.

Another preferred A-A-A-B vaccine includes hemagglutinins from: (i) a H1N1 strain, (ii) a H3N2 strain, (iii) a H5 strain (e.g. a H5N1 strain) and (iv) an influenza B strain.

Another preferred A-A-A-B vaccine includes hemagglutinins from: (i) two different H1 strains, (ii) a H3N2 strain, and (iii) an influenza B strain.

Where antigens are present from two or more influenza B virus strains, at least two of the influenza B virus strains may have distinct hemagglutinins but related neuraminidases. For instance, they may both have a B/Victoria/2/87-like neuraminidase [50] or may both have a B/Yamagata/16/88-like neuraminidase. For instance, two B/Victoria/2/87-like neuraminidases may both have one or more of the following sequence characteristics: (1) not a serine at residue 27, but preferably a leucine; (2) not a glutamate at residue 44, but preferably a lysine; (3) not a threonine at residue 46, but preferably an isoleucine; (4) not a proline at residue 51, but preferably a serine; (5) not an arginine at residue 65, but preferably a histidine; (6) not a glycine at residue 70, but preferably a glutamate; (7) not a leucine at residue 73, but preferably a phenylalanine; and/or (8) not a proline at residue 88, but preferably a glutamine. Similarly, in some embodiments the neuraminidase may have a deletion at residue 43, or it may have a threonine; a deletion at residue 43, arising from a trinucleotide deletion in the NA gene, has been reported as a characteristic of B/Victoria/2/87-like strains, although recent strains have regained Thr-43 [50]. Conversely, of course, the opposite characteristics may be shared by two B/Yamagata/16/88-like neuraminidases e.g. S27, E44, T46, P51, R65, G70, L73, and/or P88. These amino acids are numbered relative to the 'Lee40' neuraminidase sequence [51]. Thus a A-A-B-B vaccine of the invention may use two B strains that are antigenically distinct for HA (one B/Yamagata/16/88-like, one B/Victoria/2/87-like), but are related for NA (both B/Yamagata/16/88-like, or both B Victoria/2/87-like).

In some embodiments, the invention does not encompass a trivalent split vaccine containing hemagglutinin from each of A/New Caledonia/20/99 (H1N1), A/Wyoming/03/2003 (H3N2) and B/Jiangsu/10/2003 strains.

Strains whose antigens can usefully be included in the compositions include strains which are resistant to antiviral therapy (e.g. resistant to oseltamivir [52] and/or zanamivir), including resistant pandemic strains [53].

Vaccines Free from Certain Additives

The preparation of vaccines without the use of certain components and additives is disclosed in reference 54, thereby ensuring that these materials are not present even in residual amounts.

In some embodiments of the invention, a vaccine may include a small amount of mercury-based preservative, such as thiomersal or merthiolate. When present, such preservatives will typically provide less than 5 µg/ml mercury, and lower levels are possible e.g. <1 µg/ml, <0.5 µg/ml. Preferred vaccines are free from thiomersal, and are more preferably mercury-free [15,55]. Such vaccines may include a non-mercurial preservative. Non-mercurial alternatives to thiomersal include 2-phenoxyethanol or α-tocopherol succinate [15]. Most preferably, a vaccine is preservative-free.

In some embodiments, a vaccine may include a stabilising amount of gelatin e.g. at less than 0.1%. In other embodiments, however, a vaccine is gelatin-free. The absence of gelatin can assure that the vaccine is safe in the small proportion of patients who are gelatin-sensitive [56, 57].

In some embodiments, a vaccine may include one or more antibiotics e.g. neomycin, kanamycin, polymyxin B. In preferred embodiments, though, the vaccine is free from antibiotics. In some embodiments, a vaccine may include formaldehyde. In preferred embodiments, though, the vaccine is free from formaldehyde.

As mentioned above, in some embodiments a vaccine may include egg components (e.g. ovalbumin and ovomucoid), but preferred embodiments are free from egg components.

Where a vaccine is described herein as being free from any particular component, the same limitation is also disclosed in relation to patches, processes and materials of the invention.

Antigen Content

Hemagglutinin (HA) is the main immunogen in current inactivated influenza vaccines, and vaccine doses are standardised by reference to HA levels, typically measured by SRID. Existing vaccines typically contain about 15 μg of HA per strain, although lower doses can be used e.g. for children, or in pandemic situations, or when using an adjuvant. Fractional doses such as ½ (i.e. 7.5 μg HA per strain), ¼ and ⅛ have been used, as have higher doses (e.g. 3× or 9× doses [58,59]). These vaccines have a dosage volume of 0.5 ml i.e. a typical HA concentration of 30 μg/ml/strain. The trivalent INTANZA™ product contains 9 μg of HA per strain in a 0.1 ml volume i.e. a HA concentration of 90 μg/ml/strain, giving a total HA concentration of 270 μg/ml. Products of the present invention can include between 0.1 and 50 μg of HA per influenza strain per dose, preferably between 0.1 and 50 μg e.g. 1-20 μg. Ideally a product has ≤16 μg hemagglutinin per strain e.g. 1-15 μg, 1-10 μg, 1-7 μg, 1-5 μg, etc. Particular HA doses per strain include e.g. about 15, about 10, about 7.5, about 5, about 3.8, about 1.9, about 1.5, etc.

For live vaccines, dosing is measured by median tissue culture infectious dose ($TCID_{50}$) rather than HA content e.g. a $TCID_{50}$ of between $10^6$ and $10^8$ (preferably between $10^{6.5}$-$10^{7.5}$) per strain per dose.

Influenza strains used with the invention may have a natural HA as found in a wild-type virus, or a modified HA. For instance, it is known to modify HA to remove determinants (e.g. hyper-basic regions around the HA1/HA2 cleavage site) that cause a virus to be highly pathogenic in avian 5 species. The use of reverse genetics facilitates such modifications.

Vaccine Products

Vaccine products of the invention can include components in addition to the biosoluble and biodegradable matrix material and influenza vaccine antigens.

As mentioned above, vaccine products may include a detergent. The level of detergent can vary widely e.g. between 0.05-50 μg detergent perm of HA ('μg/μg'). A low level of detergent can be used e.g. between 0.1-1 μg/μg, or a high level can be used e.g. between 5-30 μg/μg. The detergent may be a single detergent (e.g. polysorbate 80, or CTAB) or a mixture (e.g. both polysorbate 80 and CTAB). Preferred detergents are non-ionic, such as polysorbate 80 ('Tween 80') or octyl phenol ethoxylate ('Triton XI 00'). Polysorbate 80 may be present at between 0.05-50 μg polysorbate 80 per μg of HA e.g. between 0.1-1 μg/μg, 0.1-0.5 μg/μg, 5-40 μg/μg, or 8-25 μg/μg.

As mentioned above, some vaccine products may include preservatives such as thiomersal or 2-phenoxyethanol, but preferred vaccines are mercury- or preservative-free.

Vaccine products may include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, etc.

Vaccine products may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

Vaccine products are preferably sterile. Vaccine products are preferably non-pyrogenic e.g. containing <1 EU (endotoxin unit, a standard measure) per dose, and preferably <0.1 EU per dose. Vaccine products are preferably gluten-free.

Vaccine products can include immunostimulatory molecules. These can be mixed with antigen before preparing a patch. Suitable classes of immunostimulatory molecule include, but are not limited to: TLR3 agonists; TLR4 agonists; TLR5 agonists; TLR7 agonists; TLR8 agonists; TLR9 agonists; and CD1d agonists. Suitable immunostimulatory molecules include, but are not limited to: imidazoquinolines such as imiquimod ("R-837") [60,61] and resiquimod ("R-848") [62], or salts thereof (e.g. the hydrochloride salts); aminoalkyl glucosaminide phosphate derivatives, such as RC-529 [63,64]; a-glycosylceramides, such as α-galactosylceramide; 'ER 804057' from reference 65; E5564 [66,67]; etc.

Methods of Treatment, and Administration of the Vaccine

Patches of the invention can be used to deliver an influenza vaccine to a subject via their skin. Thus the invention provides a method of raising an immune response in a subject, comprising the step of applying a patch of the invention to the subject's skin, such that the patch's microneedles penetrate the subject's dermis.

The invention also provides a patch of the invention for use in a method of intradermal vaccination of a subject. The invention also provides the use of (i) a biosoluble and biodegradable matrix material and (ii) an influenza vaccine selected from the group consisting of a purified influenza virus surface antigen vaccine, an influenza vaccine prepared from viruses grown in cell culture, and a monovalent influenza vaccine, in the manufacture of a medicament for raising an immune response in a subject.

Patches are suitable for administering vaccines to human or non-human animal subjects The immune response raised by these methods and uses will generally include an antibody response, preferably a protective antibody response. Methods for assessing antibody responses, neutralising capability and protection after influenza virus vaccination are well known in the art. Human studies have shown that antibody titers against hemagglutinin of human influenza virus are correlated with protection (a serum sample hemagglutination-inhibition titer of about 30-40 gives around 50% protection from infection by a homologous virus) [68]. Antibody responses are typically measured by hemagglutination inhibition, by microneutralisation, by single radial immunodiffusion (SRID), and/or by single radial hemolysis (SRH). These assay techniques are well known in the art.

Patches may be applied to the skin by simple manual application (e.g. as with a sticking plaster or with known skin patches) or may be applied using a spring-driven injector.

Vaccines prepared according to the invention may be used to treat both children and adults. Influenza vaccines are currently recommended for use in pediatric and adult immunisation, from the age of 6 months. Thus a human subject may be less than 1 year old, 1-5 years old, 5-15 years old, 15-55 years old, or at least 55 years old. Preferred subjects for receiving the vaccines are the elderly (e.g. ≥50 years old, ≥60 years old, and preferably ≥65 years), the young (e.g. ≤5 years old), hospitalised subjects, healthcare workers, armed service and military personnel, pregnant women, the chronically ill, immunodeficient subjects, subjects who have taken an antiviral compound (e.g. an oseltamivir or zanamivir compound; see below) in the 7 days prior to receiving the vaccine, people with egg allergies and people travelling abroad. The vaccines are not suitable solely for these groups, however, and may be used more generally in a population. For pandemic strains, administration to all age groups is preferred.

Preferred compositions of the invention satisfy 1, 2 or 3 of the CPMP criteria for efficacy. In adults (18-60 years), these criteria are: (1) ≥70% seroprotection; (2) ≥40% seroconversion; and/or (3) a GMT increase of ≥2.5-fold. In elderly (>60 years), these criteria are: (1) ≥60% seroprotection; (2) ≥30% seroconversion; and/or (3) a GMT increase of ≥2-fold. These criteria are based on open label studies with at least 50 patients.

Treatment can be by a single dose schedule or a multiple dose schedule. Multiple doses may be used in a primary immunisation schedule and/or in a booster immunisation schedule. Administration of more than one dose (typically two doses) is particularly useful in immunologically naive patients e.g. for people who have never received an influenza vaccine before, or for vaccinating against a new HA subtype (as in a pandemic outbreak). Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.).

Assays

The invention also provides assays for determining the amount of influenza hemagglutinin in a skin patch which comprises a biosoluble & biodegradable matrix material and an influenza vaccine. As shown below, the matrix materials do not interfere with an ELISA format and so this technique is suitable for analysing patches of the invention, particularly for quantitative analysis of HA content. A patch is first dissolved in a suitable solvent (e.g. water or an aqueous buffer) to provide a dissolved patch solution. The dissolved patch solution is then assayed by ELISA, for example by a capture ELISA comprising immobilised anti-hemagglutinin antibodies. If the patch contains a multivalent influenza vaccine then the process may involve separate assays for each valence e.g. by using strain-specific capture antibodies, one per strain.

After a patch is dissolved in a solvent the dissolved patch solution can be treated to precipitate soluble proteins e.g. by adding trichloroacetic acid (TCA), deoxycholate (DOC), acetone, methanol, chloroform, or mixtures thereof. After precipitation the proteins can be assayed; some analytical methods may first require the proteins to be re-solubilised. As shown below, precipitation in this manner can increase the recovery of protein for some analytical purposes.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x±5%.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encephalopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable prodrug.

BRIEF DESCRIPTION OF THE DRAWINGS

FIGS. 1B, 1C & 1D show individual needles from the patch shown in FIG. 1A.

FIGS. 3A and 3B shows ELISA results for antigen from two different strains. The circles show data for a trivalent vaccine. The triangles show data with a dummy patch spiked with trivalent vaccine. The squares show data for a patch with integral trivalent vaccine. The crosses show a dummy patch.

FIG. 4 shows strain-specific IgG titers after immunisations. Each of the seven triplets of bars shows titers for the three strains in the trivalent vaccine. The triplets are, from left to right: unadjuvanted injected vaccine at 0.1 μg dose; patch-administered vaccine at 0.1 μg dose; adjuvanted injected vaccine at 0.1 μg dose; unadjuvanted injected vaccine at 0.01 μg dose; patch-administered vaccine at 0.01 μg dose; adjuvanted injected vaccine at 0.01 μg dose; naïve mice.

MODES FOR CARRYING OUT THE INVENTION

Vaccine Patch Fabrication

An influenza virus vaccine was prepared using the MDCK cell culture and antigen purification techniques used for manufacturing the OPTAFLU™ product [69]. This provides a surface antigen inactivated vaccine free from mercury, antibiotics, formaldehyde, and egg-derived materials.

Bulk monovalent antigens from each of A/H1N1, A/H3N2 and B strains included a high HA concentration (200-600 μg/ml) with about 0.5% w/v Tween 80. These three bulks were mixed to give a trivalent bulk at high HA concentration. This bulk was mixed with trehalose and sodium carboxymethylcellulose, and a microneedle patch was prepared by filling a micromold with the mixture then centrifuging at 4000 rpm for 5 minutes. The centrifuged material was then dried to give the patch. Antigens were incorporated to give a final concentration per patch of 0.01 µg, 0.1 µg, 1 µg or 15 µg of HA per strain.

Figure 1A:
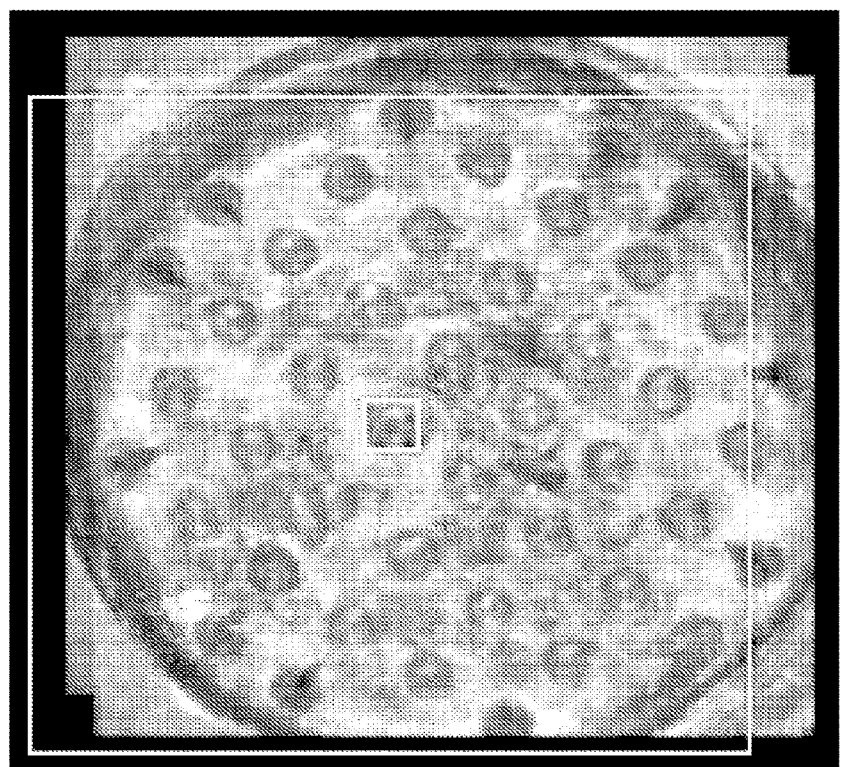
FIGS. 1A-D shows scanning electron micrograph images of a patch of the invention.
Figure 1B:
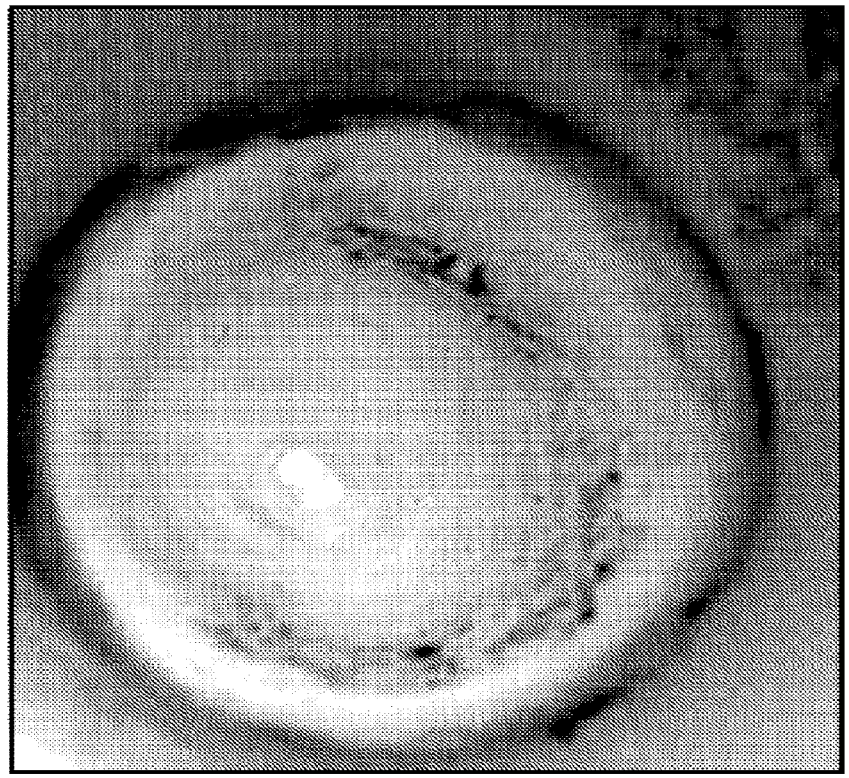
Figure 1D:
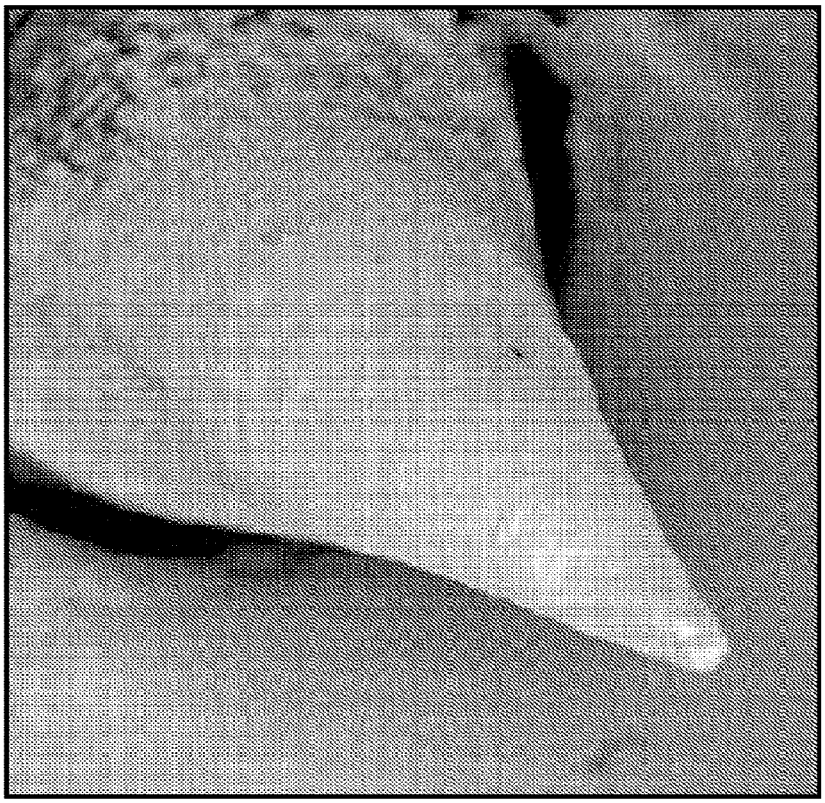
Figure 1C:
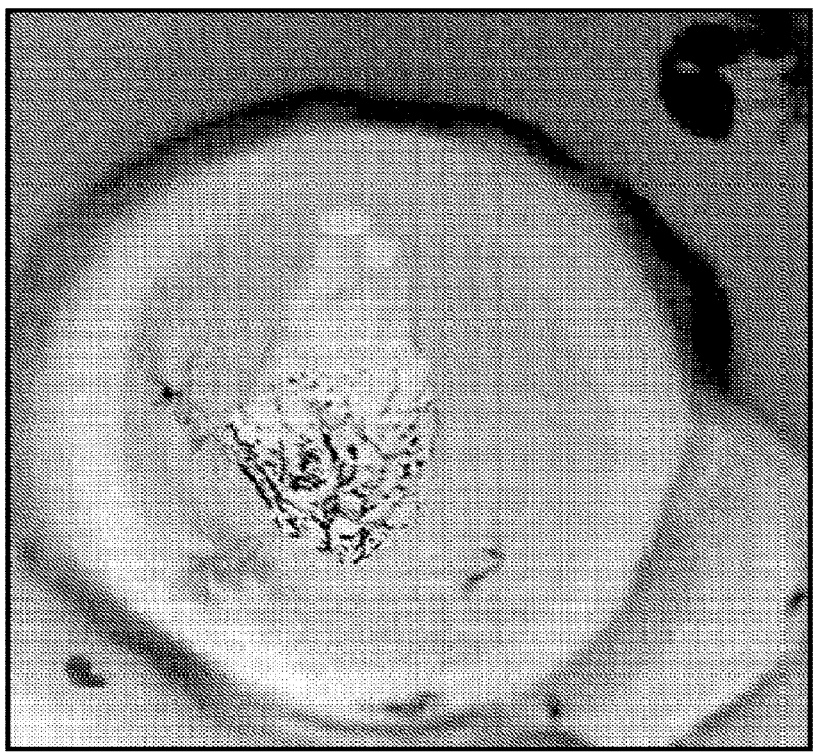
Figure 2:
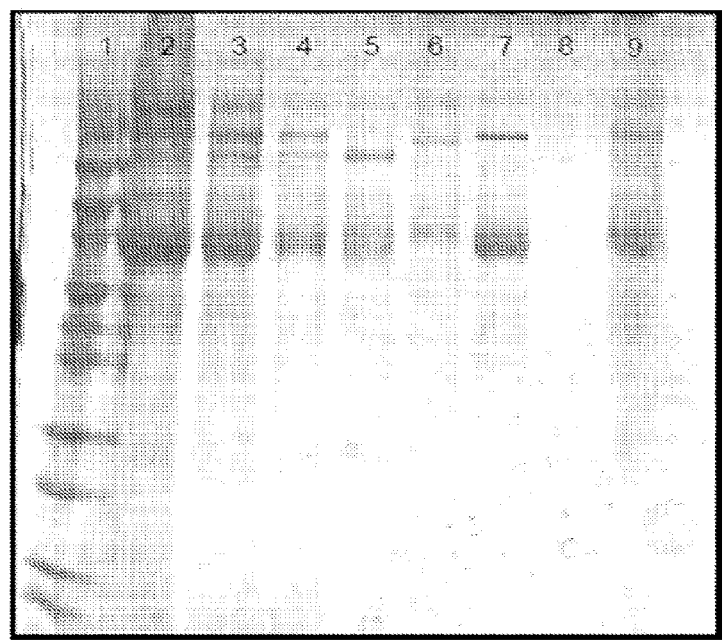
FIG. 2 shows SDS-PAGE analysis of antigens, either in solution or after formulation into a patch. Lanes are: (1) markers; (2) 3-valent antigen at 30 μg HA per strain; (3) 3-valent antigen at 15 μg HA/strain; (4) 3-valent antigen at 7.5 μg HA/strain; (5-7) monovalent HAs at 15 μg; (8) empty patch after TCA treatment; (9) patch after TCA treatment.
Figure 3A:
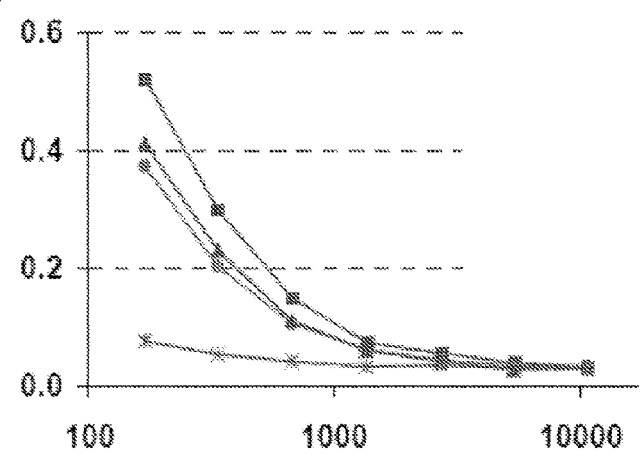
Figure 5:
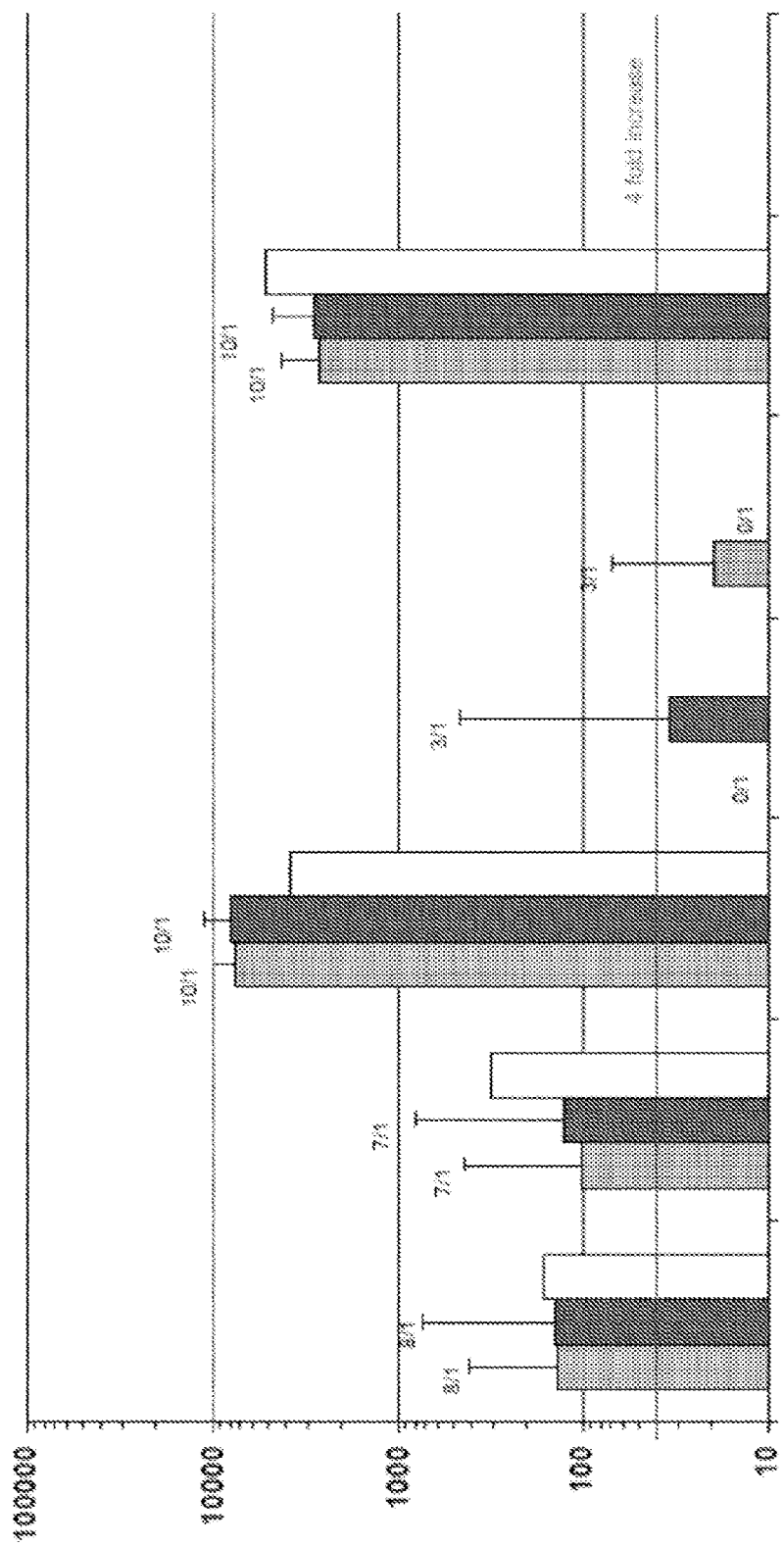
FIG. 5 shows serum H1 titers. The bars are grouped as in FIG. 4.
Figure 6:
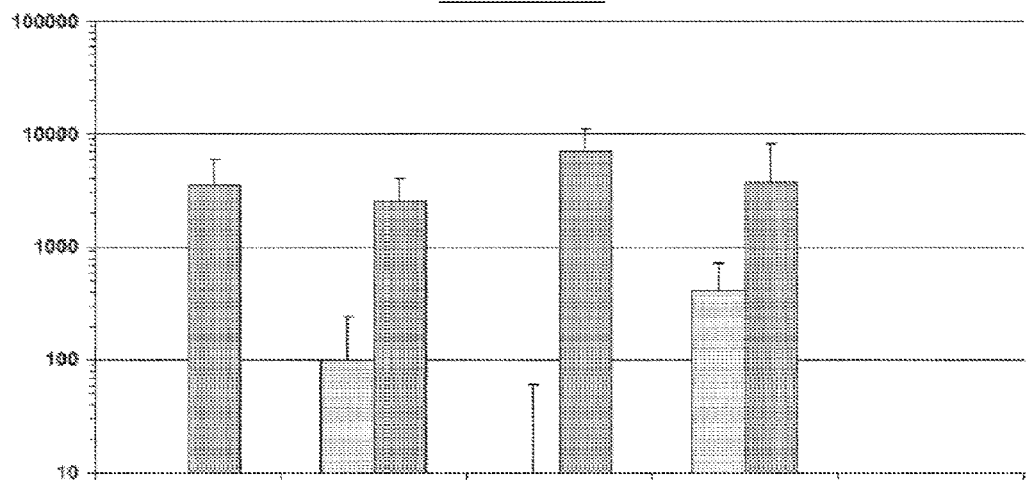
FIG. 6 shows strain-specific IgG titers. The five pairs of bars show titers after 1 dose or 2 doses. The pairs are, from left to right: unadjuvanted injected vaccine at 0.1 μg dose; patch-administered vaccine at 0.1 μg dose; unadjuvanted injected vaccine at 1 μg dose; patch-administered vaccine at 1 μg dose; mice receiving PBS alone.
Figure 7:
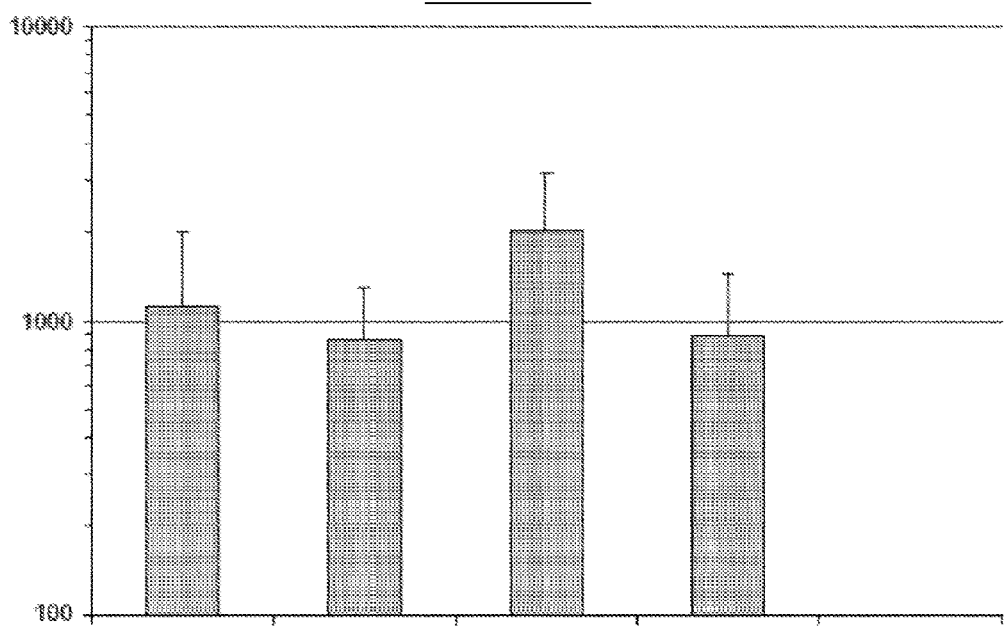
FIG. 7 shows serum HI titers against one vaccine strain. The five groups are as in FIG. 6.
Figure 8:
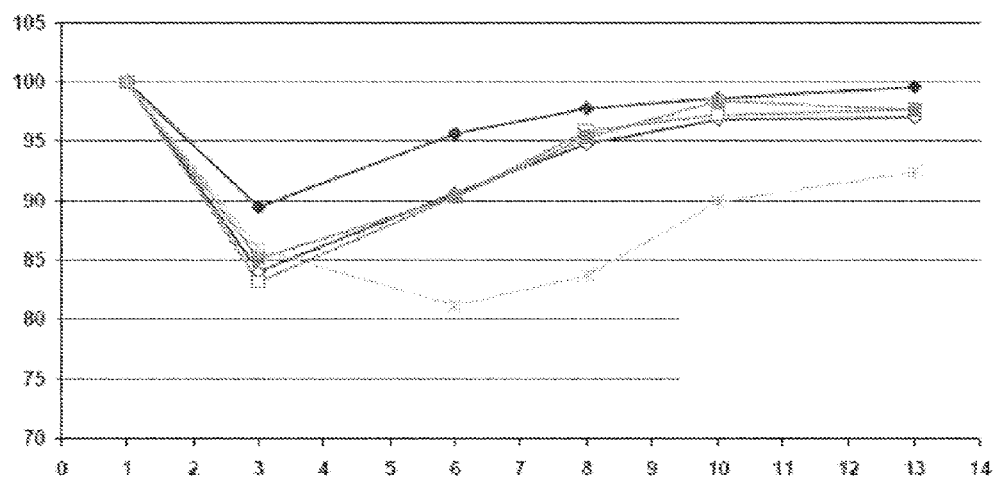
FIG. 8 shows % weight loss in mice after challenge. Diamonds show data for unadjuvanted injected vaccine at 0.1 μg (empty) or 1 μg (filled). Squares show data for patch-administered vaccine at 0.1 μg (empty) or 1 μg (filled). Crosses show data for mice receiving PBS alone.
Figure 9:
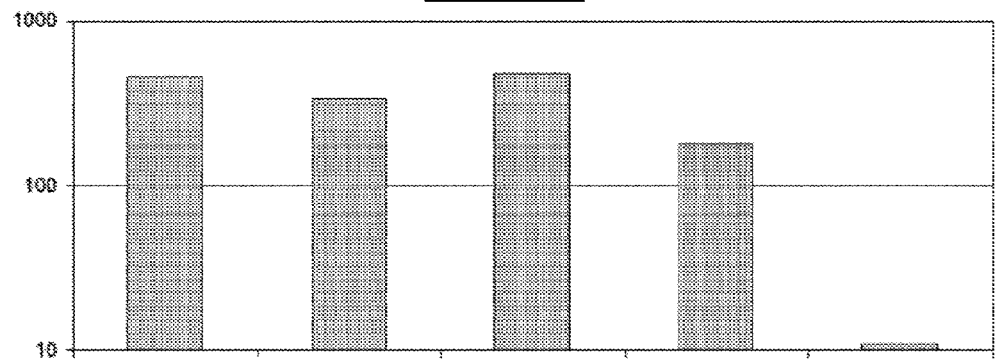
FIG. 9 shows microneutralization titers (IC80). The five groups are as in FIG. 6.

FIGS. 1A-D shows scanning electron micrographs of a patch after sputter coating with gold palladium alloy for two minutes.

Assays for Antigen in Fabricated Patches

To confirm that vaccine antigens were properly incorporated and stable, patches were characterized qualitatively by SDS-PAGE and quantitatively by capture ELISA.

Patches containing trivalent antigen at 15µ per strain were dissolved in 1 ml sterile water. Vials were vortexed for 10 minutes to ensure the entire patch was in solution. 100 μl of 0.5% deoxycholate was added to the samples. Samples were allowed to sit at room temperature for 10 minutes. After incubation 80 μl of 60% TCA was added to the sample. Samples were placed on microcentrifuge for 20 minutes at room temperature at 12 k RPM. The supernatant was removed and the pellet was dried. 60 μl of 4× reducing loading buffer and 20 μl of 1M Tris-HCl pH 8 was added to the pellet. The sample was vortexed and placed on a heating block set at 90° C. for 10 minutes. Samples were allowed to cool to room temperature and were 9 μl was added to each well in a 4-20% SDS-PAGE gel. Gels were stained overnight, de-stained in distilled water, and imaged. An antigen-free patch was treated in the same way for comparison.

FIG. 2 shows results. Lanes 2-4 contain non-patch trivalent antigen in lanes 2-4 at 2×, 1× and 0.5× the concentration in the patch. Lanes 5-7 show non-patch monovalent antigens. Lane 8 shows an antigen-free patch, and lane 9 shows the TCA-precipitated patch. The three individual antigens are clearly visible in the patch.

Antigen content of the patches was analyzed by capture ELISA. In this technique ELISA plates were coated to capture the antigen. The dissolved patches were added to the plates and incubated, followed by biotinylated IgG antibody for 30 min. Subsequently, unbound IgG and antigen was washed off and a streptavidin antibody conjugated to alkaline phosphatase was added. Antigen content was then determined by enzymatic reaction with a pNPP substrate. Absorbance was measured at 405 nm and antigen concentration was extrapolated from antigen-specific standard curves.

Results are shown in FIGS. 3A & 3B. The capture ELISA was able to recover the full antigen content from patches, confirming that the matrix excipients from the patch do not interfere with the assay.

In contrast, mass spectrometry methods were able to recover around 50% of the HA content. Recovery was calculated by comparing the area of the peak in the patch sample with the area of the peak in a standard mix sample, repeated with five different peptides for each strain. This process was performed on patches which had been treated with or without TCA to precipitate their proteins. Recovery for one strain was 17% without TCA or 43% with TCA; for another strain it was 24% without TCA or 49% with TCA. Spiking studies were also used, and recovery was again poor (ranging from 41-55% across three different strains). Thus mass spectrometry was not useful for quantifying HA in the patches, presumably due to some interference from the patch excipients.

Immunization and Challenge Studies

Patches for immunization studies had a much lower antigen content (1, 0.1 or 0.01 μg HA per strain) than the patches which were used for antigen assays (15 μg per strain).

In a first series of experiments patches were loaded at 0.1 or 0.01 μg HA per strain per patch. Patches were applied to shaved mice (female Balb/C mice, 8-10 weeks old) with pressure for 3 minutes, and then removed 15 minutes later, by which time the tips of the needles were completely dissolved. Two immunizations were carried out 30 days apart and serum samples were collected before the first immunization and two weeks after each immunization. Individual serum samples were analyzed for IgG titers by ELISA (FIG. 4) and hemagglutination inhibition (HI) titers (FIG. 5). The results of the ELISA indicate comparable IgG titers upon intramuscular injection of trivalent influenza vaccine or upon patch administration at the 0.1 g dose.

In a second series of experiments patches were loaded at 0.1 or HA per strain per dose. Mice were immunised and assayed in the same way as before. FIG. 6 shows strain-specific IgG titers, and FIG. 7 shows HI results. In addition to these assays, two weeks after the second immunization the animals were challenged with one of the wild-type vaccine strains at 10 $MLD_{50}$ (300,000 $TCID_{50}$/mice). Animals were monitored every two days for weight loss after challenge, and after 14 days neutralization titers were determined to confirm protection.

FIG. 8 shows body weight. About 10-15% weight loss was observed in the first three days after viral challenge, but mice in the treated groups recovered within a week. In contrast, untreated control group suffered a ~20% weight loss and recovered only to 97% of original weight after two weeks.

FIG. 9 shows neutralization titers, calculated as the sera dilution at which 80% of the cells are protected against virus infection. The titer is expressed as IC80 and calculated using a 4 parameter curve fitting. Administration of the vaccine via the patch at 0.1 μg dose resulted in neutralization titers slightly lower than non-adjuvanted vaccine administered intramuscularly.

In conclusion, intradermal administration of influenza vaccine by the patch induced HI titers for all three influenza strains which were comparable to those achieved by intramuscular administration of non-adjuvanted vaccine. This effect was seen with HA doses as low as 0.1 μg/strain. Additionally, ELISA results indicated comparable IgG titers. In the challenge study, both microneedle patches and non-adjuvanted influenza antigen at 0.1 and 1 μg doses resulted in positive neutralization titers.

It will be understood that the invention has been described by way of example only and modifications may be made whilst remaining within the scope and spirit of the invention.

REFERENCES

[1] *Vaccines*, (eds. Plotkin & Orenstein). 4th edition, 2004, ISBN: 0-7216-9688-0.
[2] Koutsonanos et al. (2009) *PLoS ONE* 4(e): e4773.
[3] Quan et al. (2009) *PLoS ONE* 4(9):e7152.
[4] WO2007/030477.
[5] U.S. Pat. No. 6,945,952.
[6] U.S. Pat. No. 7,211,062.
[7] Sullivan et al. (2008) *Adv Mater* 20:933-8.
[8] U.S. Pat. No. 7,182,747.
[9] Oh et al. (2006) American Association of Pharmaceutical Scientists, 2006 Annual Meeting and Exposition. *The AAPS Journal*. 8(S2). (Annual Meeting).
[10] *Intradermal Delivery of Vaccines: A review of the literature and the potential for development or use in low- and middle-income countries*. (2009) Program for Appropriate Technology in Health.

[11] WO02/28422.
[12] WO02/067983.
[13] WO02/074336.
[14] WO01/21151.
[15] WO02/097072.
[16] WO2005/113756.
[17] Huckriede et al. (2003) *Methods Enzymol* 373:74-91.
[18] WO96/37624.
[19] WO98/46262.
[20] WO95/18861.
[21] Bright et al. (2008) *PLoS ONE* 3:e1501.
[22] Crevar & Ross (2008) *Virology Journal* 5:131.
[23] WO97/37000.
[24] Brands et al. (1999) *Dev Biol Stand* 98:93-100.
[25] Halperin et al. (2002) *Vaccine* 20:1240-7.
[26] Tree et al. (2001) *Vaccine* 19:3444-50.
[27] Kistner et al. (1998) *Vaccine* 16:960-8.
[28] Kistner et al. (1999) *Dev Biol Stand* 98:101-110.
[29] Bruhl et al. (2000) *Vaccine* 19:1149-58.
[30] Pau et al. (2001) *Vaccine* 19:2716-21.
[31] WO03/076601.
[32] WO2005/042728.
[33] WO03/043415.
[34] WO01/85938.
[35] WO2006/108846.
[36] EP-A-1260581 (WO01/64846).
[37] WO2006/071563.
[38] WO2005/113758.
[39] WO2006/027698.
[40] WO03/023021.
[41] WO03/023025.
[42] WO97/37001.
[43] EP-B-0870508.
[44] U.S. Pat. No. 5,948,410.
[45] WO2007/052163.
[46] WO2008/068631.
[47] Rota et al. (1992) *J Gen Virol* 73:2737-42.
[48] GenBank sequence GI:325176.
[49] Holmes et al. (2005) *PLoS Biol.* 3(9):e300.
[50] McCullers et al. (1999) *J Virol* 73:7343-8.
[51] GenBank sequence GI:325237.
[52] Herlocher et al. (2004) *J Infect Dis* 190(9):1627-30.
[53] Le et al. (2005) *Nature* 437(7062):1108.
[54] WO2009/001217
[55] Banzhoff (2000) *Immunology Letters* 71:91-96.
[56] Lasley (2007) *Pediatric Asthma, Allergy & Immunology.* 20(3): 201
[57] Coop et al. (2008) *Int Arch Allergy Immunol.* 146(1): 85-8.
[58] Treanor et al. (1996) *J Infect Dis* 173:1467-70.
[59] Keitel et al. (1996) *Clin Diagn Lab Immunol* 3:507-10.
[60] U.S. Pat. No. 4,680,338.
[61] U.S. Pat. No. 4,988,815.
[62] WO92/15582.
[60] Johnson et al. (1999) *Bioorg Med Chem Lett* 9:2273-2278.
[60] Evans et al. (2003) *Expert Rev Vaccines* 2:219-229.
[60] WO03/011223.
[60] Wong et al. (2003) *J Clin Pharmacol* 43(7):735-42.
[60] US2005/0215517.
[60] Potter & Oxford (1979) *Br Med Bull* 35:69-75.
[60] Doroshenko & Halperin (2009) *Expert Rev Vaccines* 8:679-88.

The invention claimed is:

1. A method of raising an immune response in a subject, comprising the step of applying a skin patch comprising a plurality of solid biodegradable microneedles to the subject's skin, wherein the microneedles comprise a mixture of a biosoluble and biodegradable matrix material and a purified influenza virus surface antigen vaccine, further wherein the vaccine comprises hemagglutinin and 5-30 μg of detergent per μg of hemagglutinin and the microneedles penetrate the skin's dermis.

2. A method of raising an immune response in a subject, comprising the step of applying a skin patch comprising a plurality of solid biodegradable microneedles to the subject's skin, wherein the microneedles comprise a mixture of a biosoluble and biodegradable matrix material and a purified influenza virus hemagglutinin, wherein the amount of influenza virus hemagglutinin per patch is <16 μg per strain, further wherein the skin patch comprises 5-30 μg of detergent per μg of hemagglutinin and the microneedles penetrate the skin's dermis.

3. The method of claim 1, wherein the matrix material comprises one or more carbohydrates.

4. The method of claim 3, wherein the matrix material comprises a cellulose and/or a dextrin and/or a disaccharide.

5. The method of claim 1, wherein the microneedles are 100-2500 μm long and are tapered with a skin-facing point.

6. The method of claim 1, wherein the skin patch has >20 microneedles.

7. The method of claim 1, wherein the skin patch has an area of ≤2 cm².

8. The method of claim 1, wherein a skin-facing area of the skin patch includes an adhesive to facilitate adherence to the subject's skin.

9. The method of claim 1, wherein the detergent is polysorbate 80.

10. The method of claim 1, containing 1-15 μg of hemagglutinin per influenza virus strain.

* * * * *

UNITED STATES PATENT AND TRADEMARK OFFICE
CERTIFICATE OF CORRECTION

PATENT NO. : 9,801,935 B2  
APPLICATION NO. : 15/290349  
DATED : October 31, 2017  
INVENTOR(S) : Derek O'Hagan et al.

Page 1 of 1

It is certified that error appears in the above-identified patent and that said Letters Patent is hereby corrected as shown below:

On the Title Page

Item (73) should read:  
Assignee: Seqirus UK Limited, Berkshire (GB) and Theraject, Inc., California (US)

Signed and Sealed this  
Third Day of July, 2018

Andrei Iancu  
*Director of the United States Patent and Trademark Office*